(12) United States Patent
Fraij

(10) Patent No.: US 6,190,896 B1
(45) Date of Patent: Feb. 20, 2001

(54) ACTIVE HUMAN CELLULAR TRANSGLUTAMINASE

(76) Inventor: Bassam M. Fraij, 2401 N. Star Dr., Stillwater, OK (US) 74075

(*) Notice: Under 35 U.S.C. 154(b), the term of this patent shall be extended for 0 days.

(21) Appl. No.: 09/356,818

(22) Filed: Jul. 19, 1999

Related U.S. Application Data

(63) Continuation-in-part of application No. 08/971,208, filed on Nov. 14, 1997, now abandoned.

(51) Int. Cl.[7] .................................................. G12N 9/10
(52) U.S. Cl. ................................................ 435/193
(58) Field of Search .............................................. 435/193

(56) References Cited

U.S. PATENT DOCUMENTS

| | | | |
|---|---|---|---|
| 5,549,904 | 8/1996 | Juergensen et al. | 424/423 |
| 5,726,051 | * 3/1998 | Fraij | 435/193 |

FOREIGN PATENT DOCUMENTS

WO9212238    7/1992  (WO).

OTHER PUBLICATIONS

Schwartz et al., "Human Factor XIII from Plasma and Platelets", *Jour of Biol. Chem.*, vol. 248., No. 4, pp. 1395–1407, Feb. 1973.

Lorand et al., "A Filter Paper Assay for Transamidating Enzymes Using Radioactive Amine Substrates", *Analytical Biochemistry*, 50:623–631, 1972.

H.C. Birnhoim, "Rapid Extraction of High Molecular Weight RNA from Cultured cells and Granulocytes for Nothern Analysis", *Nucleic Acides Research*, vol. 16, No. 4, pp. 1487–1497, 1988.

Ichinose et al., "Characterization of the Gene for the A Subunit of Human Factor XIII (Plasma Transglutaminase), a Blood Coagulation Factor", *Proc. Natl. Acad. Sci. USA*. vol. 85, pp. 5829–5833, Aug. 1988.

Mary et al., "The Binding of Divalent Metal Ions to Platelet Factor XIII Modulates Its Proteolysis by Trypsin and Thrombin", *Archives of Biochemistry and Biophysics*, vol. 261, No. 1, pp. 112–121, Feb. 1988.

Marchuk et al., "Construction of T–Vectors, a Rapid and General System for Direct Cloning of Unmodified PCR Products", *Nucleic Acids Research*, vol. 19, No. 5, 199.

Phillips et al., "Primary Structure of Keratinocyte Transglutaminase", *Proc. Natl., Acad. Sci. USA*, vol. 87, pp. 9333–9337, Dec. 1990.

Piacentini et al., "The Expression of "Tissue" Transglutaminase in Two Human Cancer Cell Lines is Related with the Programmed Cell Death (Apoptosis)", *European Journal Cell Biology*, 54:246–254, 1991.

Gentile et al., "Isolation and Characterization of cDNA Clones to Mouse Macrophage and Human Endothelial Cell Tissue Transglutaminases", *The Journal of Biological Chemistry*, vol. 266, No. 1, pp. 478–483, Jan. 1991.

Nakanishi et al., "Cloning and Sequence Analysis of cDNA Clones for Bovine Aortic–Endothelial–Cell Transglutaminase", *Eur. J. Biochem.*, 202:15–21, 1991.

Greenberg et al., "Transglutaminases: Multifunctional Cross–Linking Enzymes That Stabilize Tissues", *FASEB J.*, 5:3071–3077, 1991.

Fraij et al., "A Retinoic Acid–Inducible mRNA from Human Erythroleukemia Cells Encodes a Novel Tissue Transglutaminase Homologue", *The Journal of Biological Chemistry*, vol. 267, No. 31, pp. 22616–22623, 1992.

Kim et al., "The Deduced Sequence of the Novel Protransglutaminase E (TGase3) of Human and Mouse", *The Journal of Biological Chemistry*, vol. 268, No. 17, pp. 12682–12690, 1993.

Wang et al., "Transglutaminase in Response to Hypertonic NaCl–Induced Gastric Mucosal Injury in Rats", *Gatroenterology*, vol. 104, No. 1, pp. 65–74, 1993.

Rinji Akada, "Quick–Check Method to Test the Size of Escherichia coli Plasmids", *BioTechniques*, pp. 58, 1994.

Gu et al., "Recombinant Proteins Attached to a Nickel–NTA Column: Use in Affinity Purification of Antibodies", *BioTechniques*, vol. 17, No. 2, pp. 257–262, 1994.

Grant et al., "Molecular Cloning and Characterization of a Novel Transglutaminase cDNA from a Human Prostate cDNA Library", *Biochemical and Biophysical Research Communications*, vol. 203, No. 2, pp. 1117–1123, 1994.

Nakaoka et al., "$G_h$: A GTP–Binding Protein with Transglutaminase Activity and Receptor Signaling Function", *Science*, vol. 264, pp. 1593–1596, Jun. 10, 1994.

P.M. Nielsen, "Reactions and Potential Industrial Applications of Transglutamionase. Review of Literature and Patents.", *Food Biotechnology*, 9(3), pp. 119–156, 1995.

Bassam M. Fraij, "GTP Hydrolysis by Human Tissue Transglutaminase Homologue", *Biochemical and Biophysical Communications*, 218:45–49, 1996.

Raghunath et al., "Cross–Linking of the Dermo–Epidermal Junction of Skin Regenerating from Keratinocyte Autografts", *J. Clin. Invest.*, vol. 98, No. 5, pp. 1174–1184, 1996.

Fraij et al., "A Third Human Tissue Transglutaminase Homologue as a Result of Alternative Gene Transcripts", *Biochimica et Biophysica Acta*, 1306:63–74, 1996.

(List continued on next page.)

Primary Examiner—Elizabeth Slobodyansky
(74) Attorney, Agent, or Firm—Christopher W. Corbett

(57) ABSTRACT

Known cellular transglutaminase is produced as an inactive precursor which is converted to the active species. As described herein, the active species have been identified, cloned, mass produced and purified from bacterial cells. The active transglutaminase herein are useful as a biological glue for, inter alia, adhesive strength in general surgery, clinical orthopedics, skin wound repair, tissue repair, implants, tissue or organ transplantation, stomach and duodenal ulcers, food industry, technical applications, and in applications for cellular apoptosis.

13 Claims, 6 Drawing Sheets-

OTHER PUBLICATIONS

Steinert et al., "Inactive Zymogen and Highly Active Proteolytically Processed Membrane–Bound Forms of the Transglutaminase 1 Enzyme in Human Epidermal Keratinocytes", *Biochemical and Biophysical Research Communications,* 221:101–106, 1996.

Jurgennsen et al., "A New Biological Glue for Cartilage–Cartilage Interfaces: Tissue Transglutaminase", *The Journal of Bone and Joint Surgery, Inc.,* vol. 79–A, No. 2, Feb. 1997.

Lee et al., "Purification of Human Erythrocyte Transglutaminase by Immunoaffinity Chromatography," *Preparative Biochemistry,* 16 (4):321–335, 1996.

Fraij et al., "Separation and Identification of Urinary Proteins and Stone–Matrix Proteins by Mini–Slab Sodium Dodecyl Sulfate–Polyacrylamide Gel Electrophoresis," *Clinical Chemistry,* 35 (4):658–661, 1989.

Lai et al., "C–terminal Deletion of Human Tissue Transglutaminase Enhances Magnesium–dependent GTP/ATPase Activity,", *Journal of Biological Chemsitry,* 271 (49) : 31191–31195, Dec. 06, 1996.

* cited by examiner

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1547 base pairs
      (B) TYPE: nucleic acid
      (C) STRANDEDNESS: double
      (D) TOPOLOGY: linear (ii) MOLECULE TYPE: cDNA (iii) HYPOTHETICAL: No (iv) ANTI-SENSE: No (vi) ORIGINAL SOURCE:
      (A) ORGANISM: Homo sapiens
      (G) CELL TYPE: Human blood cells (vii) IMMEDIATE SOURCE:
      (B) CLONE: TG512

(ix) FEATURE:
      (A) NAME/KEY: CDS
      (B) LOCATION: 3..1541
      (C) IDENTIFICATION METHOD: experimental
      (D) OTHER INFORMATION: product = Active Transglutaminase
          evidence = Experimental (xi) SEQUENCE DESCRIPTION: SEQ ID NO:1:

```
                                                              CC         02

ATG GCC GAG GAG CTG GTC TTA GAG AGG TGT GAT CTG GAG CTG GAG ACC          50
Met Ala Glu Glu Leu Val Leu Glu Arg Cys Asp Leu Glu Leu Glu Thr
              5                  10                  15

AAT GGC CGA GAC CAC CAC ACG GCC GAC CTG TGC CGG GAG AAG CTG GTG          98
Asn Gly Arg Asp His His Thr Ala Asp Leu Cys Arg Glu Lys Leu Val
         20                  25                  30

GTG CGA CGG GGC CAG CCC TTC TGG CTG ACC CTG CAC TTT GAG GGC CGC         146
Val Arg Arg Gly Gln Pro Phe Trp Leu Thr Leu His Phe Glu Gly Arg
     35                  40                  45

AAC TAC GAG GCC AGT GTA GAC AGT CTC ACC TTC AGT GTC GTG ACC GGC         194
Asn Tyr Glu Ala Ser Val Asp Ser Leu Thr Phe Ser Val Val Thr Gly
 50                  55                  60

CCA GCC CCT AGC CAG GAG GCC GGG ACC AAG GCC CGT TTT CCA CTA AGA         242
Pro Ala Pro Ser Gln Glu Ala Gly Thr Lys Ala Arg Phe Pro Leu Arg
65                  70                  75                  80

GAT GCT GTG GAG GAG GGT GAC TGG ACA GCC ACC GTG GTG GAC CAG CAA         290
Asp Ala Val Glu Glu Gly Asp Trp Thr Ala Thr Val Val Asp Gln Gln
             85                  90                  95

GAC TGC ACC CTC TCG CTG CAG CTC ACC ACC CCG GCC AAC GCC CCC ATC         338
Asp Cys Thr Leu Ser Leu Gln Leu Thr Thr Pro Ala Asn Ala Pro Ile
         100                 105                 110

GGC CTG TAT CGC CTC AGC CTG GAG GCC TCC ACT GGC TAC CAG GGA TCC         386
Gly Leu Tyr Arg Leu Ser Leu Glu Ala Ser Thr Gly Tyr Gln Gly Ser
     115                 120                 125

AGC TTT GTG CTG GGC CAC TTC ATT TTG CTC TTC AAC GCC TGG TGC CCA         434
Ser Phe Val Leu Gly His Phe Ile Leu Leu Phe Asn Ala Trp Cys Pro
130                 135                 140

GCG GAT GCT GTG TAC CTG GAC TCG GAA GAG GAG CGG CAG GAG TAT GTC         482
Ala Asp Ala Val Tyr Leu Asp Ser Glu Glu Glu Arg Gln Glu Tyr Val
145                 150                 155                 160
```

```
CTC ACC CAG CAG GGC TTT ATC TAC CAG GGC TCG GCC AAG TTC ATC AAG      530
Leu Thr Gln Gln Gly Phe Ile Tyr Gln Gly Ser Ala Lys Phe Ile Lys
        165                 170                 175

AAC ATA CCT TGG AAT TTT GGG CAG TTT GAA GAT GGG ATC CTA GAC ATC      578
Asn Ile Pro Trp Asn Phe Gly Gln Phe Glu Asp Gly Ile Leu Asp Ile
        180                 185                 190

TGC CTG ATC CTT CTA GAT GTC AAC CCC AAG TTC CTG AAG AAC GCC GGC      626
Cys Leu Ile Leu Leu Asp Val Asn Pro Lys Phe Leu Lys Asn Ala Gly
        195                 200                 205

CGT GAC TGC TCC CGC CGC AGC AGC CCC GTC TAC GTG GGC CGG GTG GTG      674
Arg Asp Cys Ser Arg Arg Ser Ser Pro Val Tyr Val Gly Arg Val Val
210                 215                 220

AGT GGC ATG GTC AAC TGC AAC GAT GAC CAG GGT GTG CTG CTG GGA CGC      722
Ser Gly Met Val Asn Cys Asn Asp Asp Gln Gly Val Leu Leu Gly Arg
225                 230                 235                 240

TGG GAC AAC AAC TAC GGG GAC GGC GTC AGC CCC ATG TCC TGG ATC GGC      770
Trp Asp Asn Asn Tyr Gly Asp Gly Val Ser Pro Met Ser Trp Ile Gly
                245                 250                 255

AGC GTG GAC ATC CTG CGG CGC TGG AAG AAC CAC GGC TGC CAG CGC GTC      818
Ser Val Asp Ile Leu Arg Arg Trp Lys Asn His Gly Cys Gln Arg Val
                260                 265                 270

AAG TAT GGC CAG TGC TGG GTC TTC GCC GCC GTG GCC TGC ACA GTG CTG      866
Lys Tyr Gly Gln Cys Trp Val Phe Ala Ala Val Ala Cys Thr Val Leu
        275                 280                 285

AGG TGC CTG GGC ATC CCT ACC CGC GTC GTG ACC AAC TAC AAC TCG GCC      914
Arg Cys Leu Gly Ile Pro Thr Arg Val Val Thr Asn Tyr Asn Ser Ala
        290                 295                 300

CAT GAC CAG AAC AGC AAC CTT CTC ATC GAG TAC TTC CGC AAT GAG TTT      962
His Asp Gln Asn Ser Asn Leu Leu Ile Glu Tyr Phe Arg Asn Glu Phe
305                 310                 315                 320

GGG GAG ATC CAG GGT GAC AAG AGC GAG ATG ATC TGG AAC TTC CAC TGC     1010
Gly Glu Ile Gln Gly Asp Lys Ser Glu Met Ile Trp Asn Phe His Cys
                325                 330                 335

TGG GTG GAG TCG TGG ATG ACC AGG CCG GAC CTG CAG CCG GGG TAC GAG     1058
Trp Val Glu Ser Trp Met Thr Arg Pro Asp Leu Gln Pro Gly Tyr Glu
                340                 345                 350

GGC TGG CAG GCC CTG GAC CCA ACG CCC CAG GAG AAG AGC GAA GGG ACG     1106
Gly Trp Gln Ala Leu Asp Pro Thr Pro Gln Glu Lys Ser Glu Gly Thr
        355                 360                 365

TAC TGC TGT GGC CCA GTT CCA GTT CGT GCC ATC AAG GAG GGC GAC CTG     1154
Tyr Cys Cys Gly Pro Val Pro Val Arg Ala Ile Lys Glu Gly Asp Leu
        370                 375                 380

AGC ACC AAG TAC GAT GCG CCC TTT GTC TTT GCG GAG GTC AAT GCC GAC     1202
Ser Thr Lys Tyr Asp Ala Pro Phe Val Phe Ala Glu Val Asn Ala Asp
385                 390                 395                 400

GTG GTA GAC TGG ATC CAG CAG GAC GAT GGG TCT GTG CAC AAA TCC ATC     1250
Val Val Asp Trp Ile Gln Gln Asp Asp Gly Ser Val His Lys Ser Ile
                405                 410                 415

AAC CGT TCC CTG ATC GTT GGG CTG AAG ATC AGC ACT AAG AGC GTG GGC     1298
Asn Arg Ser Leu Ile Val Gly Leu Lys Ile Ser Thr Lys Ser Val Gly
                420                 425                 430

CGA GAC GAG CGG GAG GAT ATC ACC CAC ACC TAC AAA TAC CCA GAG GGG     1346
Arg Asp Glu Arg Glu Asp Ile Thr His Thr Tyr Lys Tyr Pro Glu Gly
                435                 440                 445

TCC TCA GAG GAG AGG GAG GCC TTC ACA AGG GCG AAC CAC CTG AAC AAA     1394
Ser Ser Glu Glu Arg Glu Ala Phe Thr Arg Ala Asn His Leu Asn Lys
        450                 455                 460

CTG GCC GAG AAG GGG GAG ACA GGG ATG GCC ATG CGG ATC CGT GTG GGC     1442
Leu Ala Glu Lys Gly Glu Thr Gly Met Ala Met Arg Ile Arg Val Gly
```

```
465              470              475              480
CAG AGC ATG AAC ATG GGC AGT GAC TTT GAC GTC TTT GCC CAC ATC ACC   1490
Gln Ser Met Asn Met Gly Ser Asp Phe Asp Val Phe Ala His Ile Thr
                485              490              495

AAC AAC ACC GCT GAG GAG TAC GTC TGC CGC CTC CTG CTC TGT GCC CGC   1538
Asp Asp Thr Ala Glu Glu Tyr Val Cys Arg Leu Leu Leu Cys Ala Arg
                500              505              510

TGA CTCGAG                                                         1547
```

(2) INFORMATION FOR SEQ ID NO:2:

(i) SEQUENCE CHARACTERISTICS:
        (A) LENGTH: 512
        (B) TYPE: amino acid
        (D) TOPOLOGY: linear (ii) MOLECULE TYPE: protein (xi) SEQUENCE DESCRIPTION: SEQ ID NO:2:

```
Met Ala Glu Glu Leu Val Leu Glu Arg Cys Asp Leu Glu Leu Glu Thr
                5                  10                 15

Asn Gly Arg Asp His His Thr Ala Asp Leu Cys Arg Glu Lys Leu Val
                20                 25                 30

Val Arg Arg Gly Gln Pro Phe Trp Leu Thr Leu His Phe Glu Gly Arg
                35                 40                 45

Asn Tyr Glu Ala Ser Val Asp Ser Leu Thr Phe Ser Val Val Thr Gly
                50                 55                 60

Pro Ala Pro Ser Gln Glu Ala Gly Thr Lys Ala Arg Phe Pro Leu Arg
65                  70                 75                 80

Asp Ala Val Glu Glu Asp Trp Thr Ala Thr Val Val Asp Gln Gln
                    85                 90                 95

Asp Cys Thr Leu Ser Leu Gln Leu Thr Thr Pro Ala Asn Ala Pro Ile
                100                105                110

Gly Leu Tyr Arg Leu Ser Leu Glu Ala Ser Thr Gly Tyr Gln Gly Ser
                115                120                125

Ser Phe Val Leu Gly His Phe Ile Leu Leu Phe Asn Ala Trp Cys Pro
130                 135                140

Ala Asp Ala Val Tyr Leu Asp Ser Glu Glu Arg Gln Glu Tyr Val
145                 150                155                160

Leu Thr Gln Gln Gly Phe Ile Tyr Gln Gly Ser Ala Lys Phe Ile Lys
                165                170                175

Asn Ile Pro Trp Asn Phe Gly Gln Phe Glu Asp Gly Ile Leu Asp Ile
                180                185                190

Cys Leu Ile Leu Leu Asp Val Asn Pro Lys Phe Leu Lys Asn Ala Gly
                195                200                205

Arg Asp Cys Ser Arg Arg Ser Ser Pro Val Tyr Val Gly Arg Val Val
210                 215                220

Ser Gly Met Val Asn Cys Asn Asp Asp Gln Gly Val Leu Leu Gly Arg
225                 230                235                240

Trp Asp Asn Asn Tyr Gly Asp Gly Val Ser Pro Met Ser Trp Ile Gly
                    245                250                255

Ser Val Asp Ile Leu Arg Arg Trp Lys Asn His Gly Cys Gln Arg Val
                260                265                270

Lys Tyr Gly Gln Cys Trp Val Phe Ala Ala Val Ala Cys Thr Val Leu
                275                280                285

Arg Cys Leu Gly Ile Pro Thr Arg Val Val Thr Asn Tyr Asn Ser Ala
```

```
                    290                 295                 300
His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
                340                 345                 350

Gly Trp Gln Ala Leu Asp Pro Thr Pro Gln Glu Lys Ser Glu Gly Thr
            355                 360                 365

Tyr Cys Cys Gly Pro Val Pro Val Arg Ala Ile Lys Glu Gly Asp Leu
        370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Asp Gly Ser Val His Lys Ser Ile
                405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
            435                 440                 445

Ser Ser Glu Glu Arg Glu Ala Phe Thr Arg Ala Asn His Leu Asn Lys
        450                 455                 460

Leu Ala Glu Lys Gly Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Leu Cys Ala Arg
                500                 505                 510

(2) INFORMATION FOR SEQ ID NO:3:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TCA GCG GGC ACA GAG CAG GA                                           20
 *  Arg Ala Cys Leu Leu
    512             508

(2) INFORMATION FOR SEQ ID NO:4:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAGGCGTGAC GCCAGTTCTAA                                               21

(2) INFORMATION FOR SEQ ID NO:5:

(i) SEQUENCE CHARACTERISTICS:
        (A) LENGTH: 21 nucleotides
        (B) TYPE: nucleic acid
```

(C) STRANDEDNESS: single
        (D) TOPOLOGY: linear (ii) MOLECULE TYPE: cDNA (xi) SEQUENCE DESCRIPTION: SEQ ID NO:5:

```
TCA GCC CAC ACG GAT CCG CAT                                              21
 *  Gly Val Arg Ile Arg Met
    480             475
```

(2) INFORMATION FOR SEQ ID NO:6:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
TCA TTT GTT CAG GTG GTT                                                  18
 *  Lys Asn Leu His Asn
    464         460
```

(2) INFORMATION FOR SEQ ID NO:7:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TCA TGG GTA TTT GTA GGT GTG                                              21
 *  Pro Tyr Lys Tyr Thr His
    446             441
```

(2) INFORMATION FOR SEQ ID NO:8:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
ACCTCCTTAA AGCATAAATC TCA                                                23
```

(2) INFORMATION FOR SEQ ID NO:9:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ATG GCC GAG GAG CTG GT                                                   17
Met Ala Glu Glu Leu
 1           5
```

(2) INFORMATION FOR SEQ ID NO:10:

```
    (i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCC TTA GGC GGG GCC AA                                              17
  *  Ala Pro Gly
     687
```

ACTIVE HUMAN CELLULAR TRANSGLUTAMINASE

CROSS-REFERENCE TO RELATED APPLICATIONS

The present application is a continuation-in-part of U.S. Ser. No. 08/971,208, filed Nov. 14, 1997, now abandoned entitled "Active Human Cellular Transglutaminase," the specification of which is incorporated by reference herein in its entirety.

STATEMENT REGARDING FEDERALLY SPONSORED RESEARCH OR DEVELOPMENT

Not Applicable

BACKGROUND

Transglutaminases are a calcium dependent family of enzymes responsible for post-translational crosslinking of proteins. The crosslinked protein products are large chemically, enzymatically, and mechanically resistant polymers with a variety of functions ranging from wound healing to skin formation (Greenberg et al., FASEB J. 5: 3071–3077 (1991)).

To date, there are several human transglutaminases which are produced from different genes. The catalytic subunit of blood-clotting factor XIIIa, or plasma transglutaminase, is 80 kDa (Ichinose et al., Proc. Natl. Acad. Sci. USA 85: 5829–5833 (1988)), the epidermal keratinocyte transglutaminase is 106 kDa (Phillips et al., Proc. Natl. Acad. Sci. 87: 933–9337 (1990)), the epidermal and hair follicle transglutaminases are 77 kDa (Kim et al., J. Biol. Chem. 268: 12682–12690 (1993)), the prostate transglutaminase is 78 kDa (Grant et al., Biochem. Biophys. Res. Comm. 203: 117–1123 (1994)), and the cellular transglutaminase is about 80 kDa (Gentile et al., J.Biol.Chem. 266: 478–483 (1991)).

Molecular cloning of cDNA for different forms of the cellular transglutaminase were reported (Gentile et al., J. Biol. Chem. 266:478–483 (1991), and a patent application number WO 92/12238), Fraij et al., J. Biol. Chem. 267: 22616–22673 (1992), and U.S. Pat. No. 5,726,051, Fraij and Gonzales, Biochim. Biophys. Acta. 1306: 63–74 (1996)). The complete organization and structure of a human cellular transglutaminase gene was recently published (Fraij and Gonzales, Biochim. Biophys. Acta. In Press (1997)).

Cellular transglutaminase is one of the most extensively studied of the transglutaminases and its crosslinking activities have been reported to be involved in skin wound healing, adhesive strength at the cartilage-cartilage interface and in the gastric mucosal injury healing (Raghunatg et al., J. Clin. Invest. 98: 1174–1184 (1996), Jurgensen et al., J. Bone and Joint Surg. 79-A: 185–193 (1997), Wang et al., Gastroenterology 104: 65–74 (1993)). Cellular transglutaminase crosslinking activities have been reported to be involved in the stabilization of apoptotic bodies (Piacentini et al., Eur. J. Cell Biol. 54: 246–254 (1991)), and to function in cellular signal transfer as a GTP receptor coupling protein (Nakaoka et al., Science 264: 1593–1596 (1994)).

Transglutaminase homologue was found recently to bind and hydrolyze GTP several fold more than the cellular transglutaminase, activities which may be related to the events of cell signaling (Fraij, Biochem. Biophys. Res. Comm. 218: 45–49 (1996)). Transglutaminase crosslinking reactions are known to occur early in regulation of receptor/membrane functions. It is evident from the patent literature that numerous concepts have been tested and are believed to have a future in the industry, however this will very much depend upon the availability and costs of the transglutaminase.

Cellular transglutaminase when compared to the other known transglutaminases, except for cellular transglutaminase, all were reported to exist as zymogen and require a limited proteolysis for full enzyme activity (Greenberg et al., FASEB J. 5: 3071–3077 (1991)). Since its discovery in 1954, the 80 kDa form of cellular transglutaminase is regarded as the active enzyme and often cited as the enzyme of the family that does not require proteolytic activation.

Transglutaminases have been used for crosslinking purposes in a variety of fields. Currently, Factor XIIIa purified from human plasma and placenta are used for intravenous injections to treat chronic venous ulcerations and as a fibrin sealant for surgery purposes. Microbial transglutaminases have found use in food industry, and since 1993 have been commercially available in Japan.

Human Factor XIIIa requires some form of activation to become catalytically active, and as each transglutaminase has certain substrates, their activities may be limited in certain applications. Therefore, what is needed in the art are methods for producing by recombinant means human transglutaminase which is catalytically active and does not require activation and does not require testing for HIV and Hepatitis viruses.

SUMMARY OF THE INVENTION

The present invention provides the ability to mass produce active cellular transglutaminase and polypeptides or fragments thereof by recombinant means in bacterial cells. Accordingly, isolated and purified polynucleotide constructs are described which code for the active transglutaminase.

In the hundreds of papers on cellular transglutaminase published since its discovery in 1954, the 80 kDa form is regarded as the active enzyme. It is often cited as the enzyme of the family that does not require proteolytic activation. However, this invention provides evidence that the 80 kDa polypeptide is an inactive precursor and can be converted in vitro and in vivo proteolytically to produce form(s) with a molecular weight of about 55 kDa, which are the active species in crosslinking reactions as summarized in this equation:

Human Cellular Transglutaminase(RBC)→Human Cellular Transglutaminase Inactive. Full length about 80 kDa Fully active, partially cleaved, about 55 kDa In related embodiments the invention concerns DNA constructs which encode crosslinking active transglutaminase or fragment thereof, and a translational terminator, each operably linked for expression of the active enzyme. The constructs are used to transform or transfect host cells, preferably bacterial cells. The expressed active transglutaminase was purified from the bacterial cells by affinity purification.

Nucleic acid sequences of the constructs which encode the active transglutaminase of the invention and the recombinant transglutaminase itself can also be used to develop compounds which can alter transglutaminase associated apoptosis of eucaryotic cells. Antibodies raised against the active transglutaminase can be used for screening of apoptosis and for testing compounds which can act as agonists or antagonists of apoptosis-mediated mechanisms.

Western blot analysis was performed as described in Example (1). Prestained markers (lane 1), RBC membrane protein (MP) with no trypsin (lanes 2 and 5), MP with 5 mM CaCl$_2$ and trypsin for 1 and 6 min (lanes 3 and 4), MP with 0.3 mM GTP and trypsin for 1 and 6 min (lanes 6 and 7).

Figure 2:
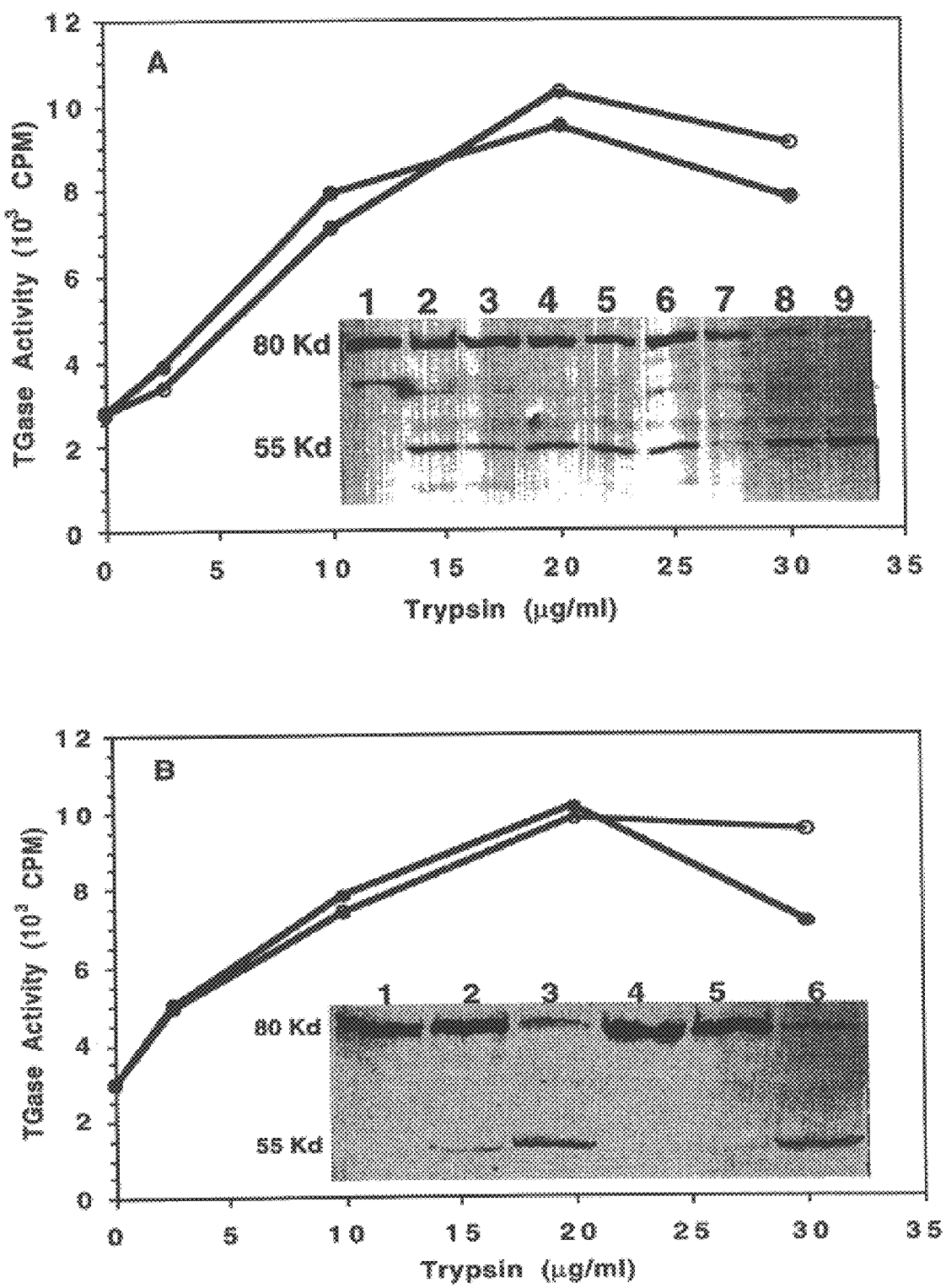

FIG. 2 illustrates the cellular transglutaminase activation by proteolysis: effect of trypsin concentration on transglutaminase activation of membranes from human RBC (A), and human erythroleukemia cells-K562 (B). Insert A) RBC membranes with no trypsin addition (lane 1), transglutaminase digestion by increasing concentrations of trypsin as indicated on the abscissa for each time point assayed and in presence of 5 mM CaCl$_2$ (lanes 7, 6, 8, and 9) or 0.3 mM GTP (lanes 3, 2, 4, and 5). B) K562 membranes in the presence of 5 mM CaCl$_2$ (lanes 1, 2, and 3) or 0.3 mM GTP (lanes 4, 5, and 6), no trypsin (lanes 1 and 4), 2.5 μg/ml trypsin (lanes 2 and 5), and 20 μg/ml trypsin (lanes 3 and 6).

Figure 3:
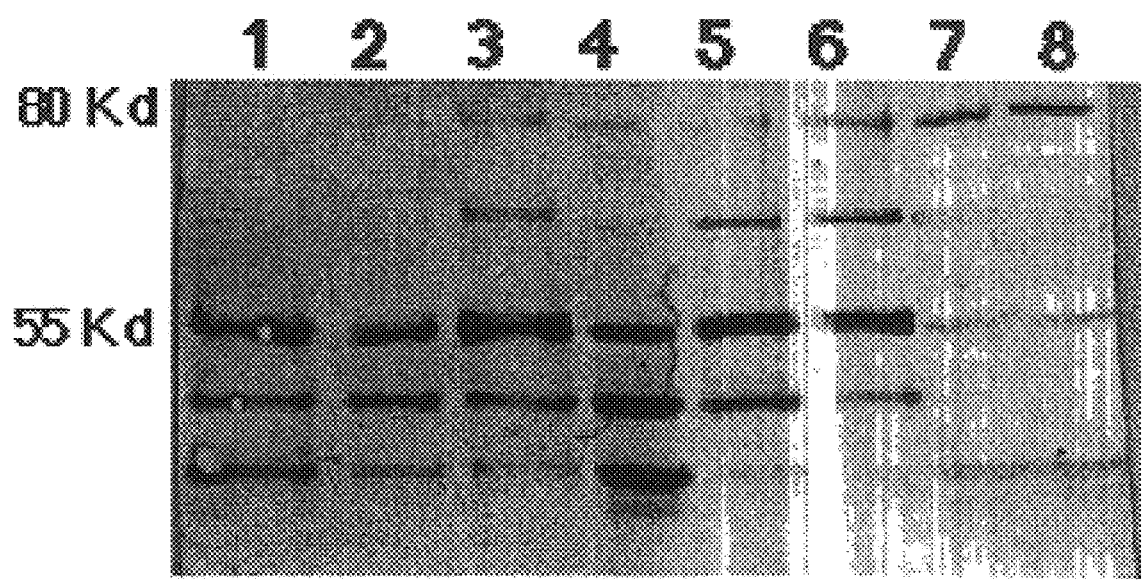

FIG. 3 illustrates the effect of time on the proteolysis of purified transglutaminase. Immunoblot of purified RBC transglutaminase digested with trypsin for 6, 3, and 1 min in the presence of 5 mM CaCl$_2$ (lanes 1, 2, and 3), or in the presence of 0.3 mM GTP (lanes 4, 5 and 6). Purified RBC transglutaminase without trypsin (lane 7, with calcium and lane 8, with GTP).

Figure 4:
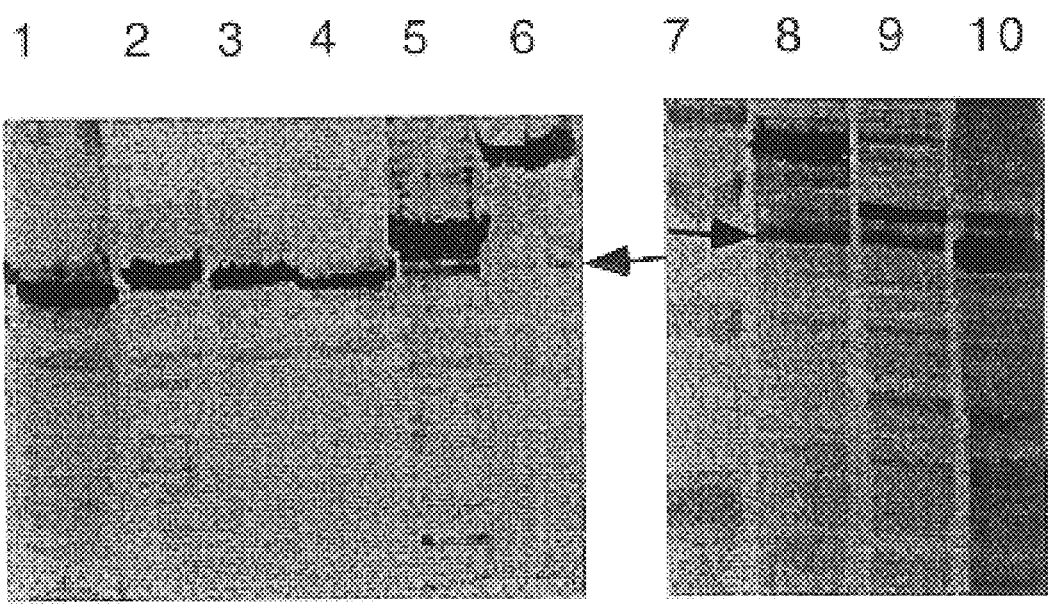

FIG. 4. Western blot analysis of bacterially expressed transglutaminase isoforms. Bacterial lysate supernatants from pET containing inserts of TG446, TG512, TG480, TG464, TGH, and TGC (Lanes 1, 2, 3, 4, 5, and 6), and pRSET containing insert of TGC, TGH, and TG. (Lanes 8, 9, and 10). Prestain markers of 107, 76, 52, 36 kDa molecular weights (Lane 7). Top arrow indicate the TG protein formations from TGC and TGH in the pRSET expressions (Lanes 8 and 9). Bottom arrow indicate the TG native protein formation from pET expression constructs.

Figure 5:
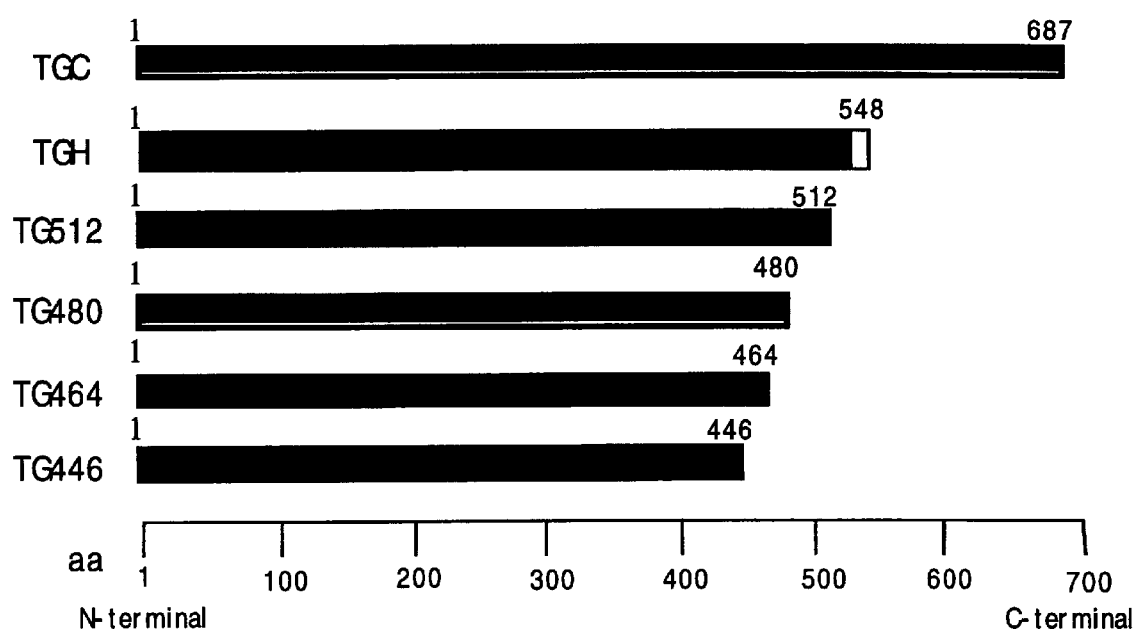

FIG. 5. Schematic illustration of the transglutaminase polypeptide forms found. Solid black represents shared amino acid sequences. White represents alternative amino acid sequences. Molecular weights of TGC and TGH are about 80 and 63 kDa, and the TG forms are about 51 to 58 kDa.

Figure 6:
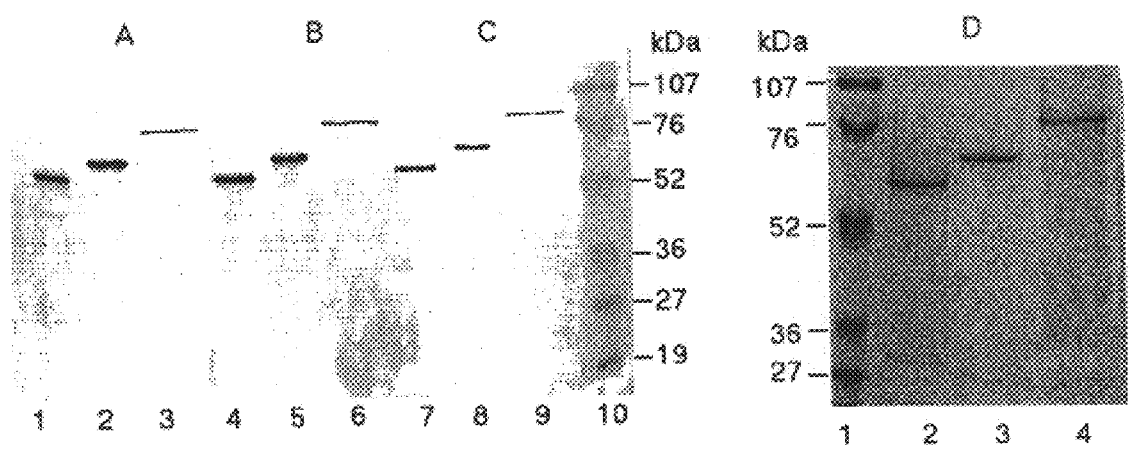

FIG. 6 illustrates the immunodetection of the purified TG, TGH, and TGC isoforms by Western blot. A (TG-polyclonal antibody), B (TGC-polyclonal antibody), and C (TGC-monoclonal antibody). Coomassie Brilliant Blue (CBB) gel staining (D) of TG (lane 2), TGH (lane 3), and TGC (lane 4). Pre-stained molecular weight markers (lanes 10 and 1).

DESCRIPTION OF THE PREFERRED EMBODIMENTS

Cellular transglutaminase catalyzes the covalent crosslinking of proteins by forming ε-(γ-glutamyl)lysine isopeptide linkages that are used for different cellular and extracellular functions. The present invention provides isolated nucleotide sequences (cDNAs) which express the active human cellular transglutaminase with a molecular weight of about 55 kDa (TG). The recombinant enzyme was purified to homogeneity and found to be very active in crosslinking reactions. The invention provides that the native cellular transglutaminase with a molecular weight of 80 kDa (TGC) and the transglutaminase homologue with a molecular weight of 63 kDa (TGH) are produced in cells as zymogens and they are inactive in crosslinking reactions. The TGC and TGH forms can be converted proteolytically to the active TG forms.

The invention also provides the production of recombinant active TG forms in bacterial cells which forms are purified, assayed for crosslinking activity, and shown to be the active species of cellular transglutaminase.

As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion and insertion mutations.

It is also contemplated, as noted above, that the polypeptide of the present invention may comprise minor variation in the amino acid residues therein as long as the variations do not sub-stantially reduce the crosslinking activity of the transglutaminase enzyme described and claimed herein.

Generally, these variations comprise conservative substitutions. By conservative substitution is meant an amino acid residue replaced with another which is biologically and/or chemically similar, e.g., one hydrophobic residue for another, or one polar residue for another. The substitution include combinations such as Gly, Ala; Val, Ile Leu, Met; Asp, Glu; Asn, Gln; Ser, Thr; Lys, Arg; and Phe, Tyr.

Amino acid substitutions are typically of single residues. Wherein at least one residue has been removed and a different residue inserted in its place. Such substitutions generally are made in accordance with the following Table 1.

TABLE 1

| Original Residue | Exemplary Substitution |
|---|---|
| Ala | ser |
| Arg | lys |
| Asn | gln; his |
| Asn | glu |
| Cys | ser |
| Gln | asn |
| Glu | asp |
| Gly | ala |
| His | asn; glu |
| Ile | leu; val |
| Leu | ile; val |
| Lys | arg |
| Met | leu; ile |
| Phe | met; leu; tyr |
| Ser | thr |
| Thr | ser |
| Trp | tyr |
| Tyr | trp; phe |
| Val | ile; ile |

Nucleic acid sequences encoding human cellular transglutaminase as described herein can be cloned from a variety of human cell sources as this enzyme is found in nearly all tissues. As will be appreciated by those skilled in the art, techniques are available to develop RNA and cDNA isolation protocols that use a small amount (less than 100 μl) of human whole blood as starting material by coupled reverse transcription and PCR amplification (RT-PCR). For expression cDNA are generally preferred because they lack introns that can interfere with expression. To obtain the active human cellular transglutaminase, total RNA from human blood cells was amplified by RT-PCR and the produced cDNA product was directly cloned to T-vector constructed from EcoRV digested pBluescript II as described previously (Marchuk et al, Nucleic. Acids. Res. 19: 1154 (1991)). Sources from which total RNA or mRNA may be prepared to obtain the active cellular transglutaminase of this invention consist of cells from human or animal bodies and cells grown in tissue culture and cellular products including many organs and cell types such as white blood cells (e.g.macrophages), erythrocytes (sickle cells), liver, lung, heart, kidney, spleen, endothelial cells, bone, etc.

Figure 1:
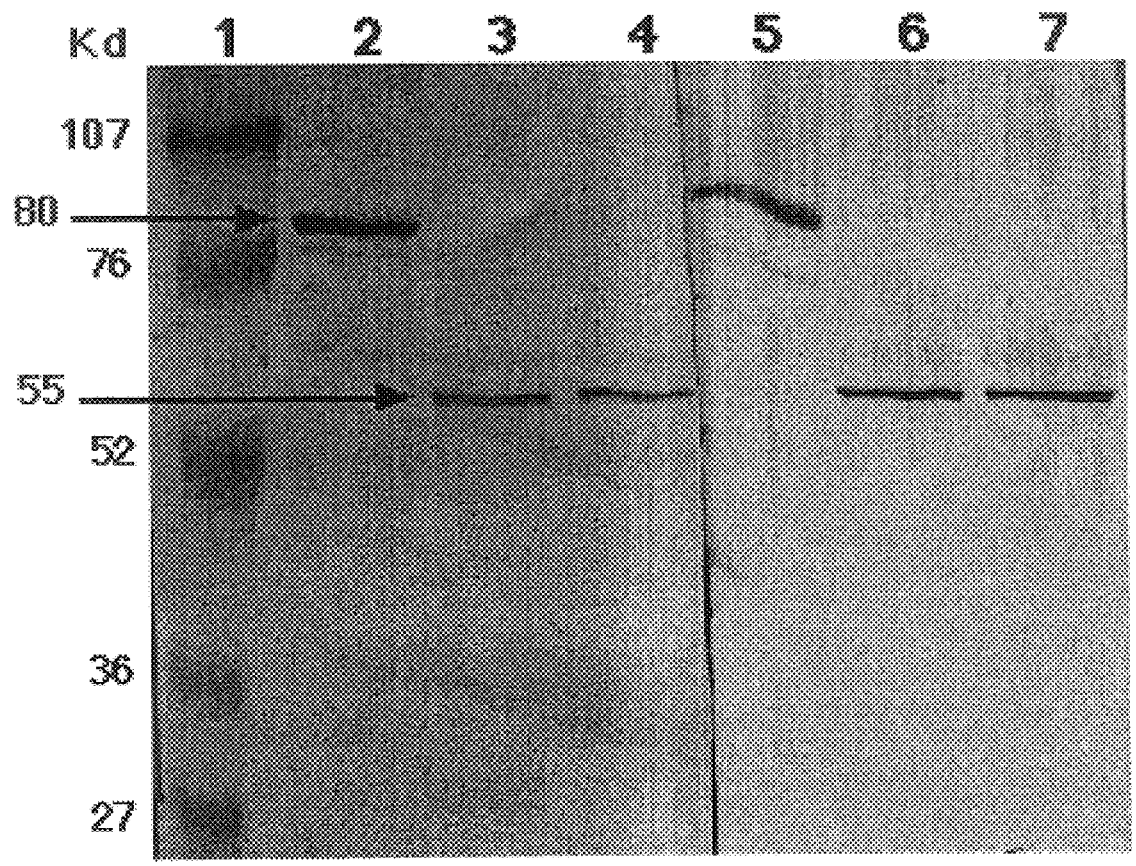
FIG. 1 illustrates the conversion of the native cellular transglutaminase from human red blood cell membranes.

Western blot analysis of transglutaminase from human red blood cell membrane proteins which were left on bench at room temperature for overnight revealed that the cellular transglutaminase (TGC) was converted to smaller forms. To understand the nature of the conversion, human RBC proteins were examined for the effect of proteolysis of transglutaminase. RBC membrane and supernatant proteins were isolated from outdated human blood (American Red Cross, Tulsa, Okla.) as shown in Example (1). Several proteolytic enzymes (commercially available) were used which included trypsin, pepsin, papain, cathepsin, and thrombin. Following proteolysis samples were immediately subjected to SDS-PAGE and immunodetection to asses transglutaminase cleavage. Only trypsin resulted in the conversion of TGC to TG polypeptides in the membrane but not in the supernatant fractions when compared to other proteolytic enzymes in the assay condition used. Calcium or GTP when included in the proteolysis reaction resulted in near-complete conversion as shown in FIG. 1.

The transglutaminase proteolytic conversions were examined for crosslinking activation in isolated membranes from human RBC and human erythroleukemia cells (K562) with increasing concentrations of trypsin. In the presence of calcium ions or GTP, there was a linear increase in the formation of TG polypeptide band with increasing concentrations of trypsin (FIG. 2). Simultaneously, there was a parallel increase in the transglutaminase crosslinking activity, thus the conversion of the TGC to the TG forms show an activation process for the transglutaminase enzyme (FIG. 2).

When the proteolytic activation of cellular transglutaminase was compared to the five known cellular transglutaminases, except for cellular transglutaminase, all were reported to exist as zymogens and require a limited proteolysis for full enzyme activity. Examples of that a) Blood coagulation Factor XIIIa is a plasma transglutaminase that is produced as a zymogen (80 kDa) and its activation occurs through thrombin cleavage of a peptide bond near the amino terminus. Both thrombin and trypsin were reported to first activate and then inactivate blood coagulation Factor XIIIa (80 kDa) by cleaving the a-chain to 56 and 24 kDa fragments (Schwartz et al, J. Biol. Chem. 248: 1395–1407 (1973)). Another study reported that digestion of Factor XIIIa with thrombin or trypsin in the presence of metal ions generated a 51-kDa polypeptide that expressed transglutaminase activity (Mary et al, Ach. Bioch. Biophys. 261: 112–121 (1988)).

b) Recently keratinocyte or type 1 transglutaminase (106 kDa) was found as an inactive zymogen in proliferating cells (Steinert et al, Biochem. Biophys. Res. Comm. 221: 101–106 (1996)). During differentiation, up to 50% is proteolytically processed into 67, 33 and 10 kDa fragments at conserved sequence sites, which are held as a 67/33/10 kDa complex, or free 67 kDa as a very active form. The mechanism of the intracellular proteolytic cleavage (processing) and activation of transglutaminase is not known.

The human cellular transglutaminase (TGC) has been extensively identified and studied. There are several reports about purification of catalytically active human tissue transglutaminase from different tissues, and all these reports indicated that the transglutaminase activity was found in a single enzyme form with about 80 kDa molecular weight.

Transglutaminase from the outdated human blood RBC was purified by QA-cellulose and immunoaffinity chromatography as I described earlier (Fraij, Biochem. Biophys. Res. Comm.218: 45–49 (1996)). The purified transglutaminase was catalytically active (Table 2), and western analysis showed that TGC was the major form and other species containing a minor form with a molecular weight of about 55 kDa (TG) was also present, (FIG. 3, lanes 7 and 8). Thus the TG form is found naturally in the human RBC. This TG minor protein band usually is not detected by a weak titer antibody or ignored because of its weak signal and is considered a result of non-specific binding in immunodetection.

In the presence of calcium or GTP (FIG. 3, lanes 1–6), trypsin rapidly degraded the purified TGC to low-molecular mass peptides (55-kDa and smaller). Thus, membrane association of transglutaminase as shown in FIGS. 1 and 2 protected it against rapid degradation.

Based on these results, I predicted that the TG isoform is formed by cleavage of the TGC form at certain residue(s). The following calculations were based on a standard and known measurements of proteins:

Amino acid residue molecular weight average=115 Da (Daltons)

Main form of transglutaminase (TGC) molecular weight= 80 Kilo Daltons (kDa)

New form of transglutaminase (TG) molecular weight=55 kDa

Therefore: 80–55=25 kDa peptide was removed.

25000 Da when divided by 115 Da resulted in about 217 amino acids which were removed. Since the active site cysteine of transglutaminase is located at residue 277, the cleavage can not take place at the N-terminus, and the cleavage must be from the C-terminus of TGC. The amino acid length for the known TGC forms are: Human and Bovine=687, Rat=686, and Mouse=685. As an average I used 686 amino acids for TGC, therefore, 217 amino acids were subtracted from 686, the resultant 469 amino acid polypeptide is the size I predicted for the new active TG transglutaminase species.

The amino acid sequence which spans the area between residues 445 to 512 of SEQ ID NO:2 was found to be similar in transglutaminases from human and mouse (Gentile, et al., J. Biol. Chem. 266: 478–483 (1991)), and bovine (Nakanishi, et al., Eur. J. Biochem. 202: 15–21 (1991)).

I designed primers for amplification the coding sequences which end at the underlined residues, with a translational stop codon and a restriction site for XhoI and or Nde I for cloning purposes in the down stream primer. By using RT-PCR amplifications of total RNA isolated from human blood cells as shown in Example (2), the produced DNA products were cloned. Cloned cDNA constructs were sequenced and found to contain the expected designed nucleotides. Comparison of bacterially expressed transglutaminase construct ends at the carboxyl side of under-lined residues 464 and 480 produced the fully active cellular transglutaminase (Table 2). The cDNA sequences of the previously reported transglutaminases and the new active transglutaminases of this disclosure (SEQ ID NO:1) were determined to be nearly identical. Only few base changes were found which possibly arose as a result of combination of polymorphisms and Taq polymerase errors. Comparison of the deduced amino acid sequences for the previously reported TGC, TGH, and the new TG forms (SEQ ID NO:2) revealed that the TGH species shares with the TG forms only the properties that they are smaller than the TGC species and have identical N-terminal amino acid sequences. The TGH form is produced in vivo by alternate RNA splicing, so that the TGH and TGC forms are not entirely colinear in amino acid sequence. In contrast, the TG and TGC forms are colinear in amino acid sequence. The removal of a carboxyl terminal peptide is required for the activation of tissue transglutaminase zymogens, which results in a unique size of active species (FIG. 5). To my knowledge, no transglutaminase of this size or proteolytic activation process for human cellular transglutaminases have been reported. The active site region residues 274–280 including cysteine 277 and the potential calcium binding region between 446–453 amino acids are present in the TG active forms.

Several expression vectors were found to be suitable for producing the active cellular transglutaminase (FIG. 4) including the pET (Novagen) and pRSET (Invitrogen). To determine whether the removal sites at Lysine 464 or Glycine 480 were the only sites required to produce the active form, other constructs between lysine 464 and glycine 480 were synthesized and also shown to produce the active forms (e.g.alanine 466). The putative calcium binding site is located between residues 446–452 and the removal of carboxyl end sequences beyond the calcium binding domain is required for the activation mechanism as shown by bacterial expression of constructs with carboxyl ends at lysine 465 to glycine 480 with molecular weights of about 53 to 55 kDa. The removal of the carboxyl end peptide possibly exposes the binding domain for the binding of calcium ions. Construct codes for TG which ended at proline 446 with a molecular weight of about 51 kDa (FIG. 5), produced a weak crosslinking activity, therefore the removal of carboxyl-terminal peptide at the calcium binding domain residue 446 interfered with the enzyme activity. Construct codes for TG which ended at arginine 512 with a molecular weight of about 58 kDa also produced a weak crosslinking activity (Table 2), which indicates that the longer the peptide extends past the calcium binding domain, the less is the enzymatic activity, possibly because the folding back of such peptide and masking this region for binding calcium ions.

The present invention comprises an isolated and purified transglutaminase enzyme having crosslinking activity and having a molecular weight of about 51 kDa to about 58 kDa, and more preferably from about 52 kDa to about 57 kDa, and more preferably from about 53 kDa to about 55 kDa.

It is further intended, therefor, that the present invention contemplates any of the polypeptides having amino acids 1–446, 1–447, 1–448, 1–449, 1–450, 1–451, 1–452, 1–453, 1–454, 1–455, 1–456, 1–457, 1–458, 1–459, 1–460, 1–461, 1–462, 1–463, 1–464, 1–465, 1–466, 1–467, 1–468, 1–469, 1–470, 1–471, 1–472, 1–473, 1–474, 1–475, 1–476, 1–477, 1–478, 1–479, 1–480, 1–481, 1–482, 1–483, 1–484, 1–485, 1–486, 1–487, 1–488, 1–489, 1–490, 1–491, 1–492, 1–493, 1–494, 1–495, 1–496, 1–497, 1–498, 1–499, 1–500, 1–501, 1–502, 1–503, 1–504, 1–505, 1–506, 1–507, 1–508, 1–509, 1–510, 1–511, and 1–512 of SEQ ID NO:2 or sequences of DNA which encode said sequences of SEQ ID NO:2.

TABLE 2

Transglutaminase activity was determined by the incorporation of 1,4-$^{14}$C-putrescine into dimethylcasein using 20 μl of supernatant from bacterial lysates (1 μg/1 μl).

| Bacterially expressed Human transglutaminase isoforms | Crosslinking Activity (CPM/hr) |
|---|---|
| TGC (pRSET) | 3990 |
| TGC (pET) | 950 |
| TGH (pRSET) | 4360 |

TABLE 2-continued

Transglutaminase activity was determined by the incorporation of 1,4-$^{14}$C-putrescine into dimethylcasein using 20 μl of supernatant from bacterial lysates (1 μg/1 μl).

| Bacterially expressed Human transglutaminase isoforms | Crosslinking Activity (CPM/hr) |
|---|---|
| TGH (pET) | 2800 |
| TG(464 or 480) (PRSET) | 20080 |
| TG(464 or 480) (pET) | 28860 |
| TG446 (pET) | 760 |
| TG412 (pET) | 560 |

Assay measurements of transglutaminases from bacterially expressed TGC and TGH preparations which were induced for 5 h with IPTG as described in Example 3, produced crosslinking activities (Table 2). These activities are proportional to the amounts of the formation of the active TG form as shown by Western analysis of these samples where the major TGC and TGH bands and a minor TG band present in the products (FIG. 4). Under the assay condition used of 20 μg total bacterial lysates from the different constructs which contains variable amount of the active TG form, therefore, constructs containing the TG (464 or 480) produced the highest amount of radioactive incorporation as a result of the presence of the full active enzyme in larger quantities when compared to TG formation from the larger precursors in the TGC and TGH constructs.

Preferably, the present transglutaminase has crosslinking activity of from at least about 1000 to about 1500 cpm/hr/μg of bacterial lysate where crosslinking activity is based on incorporation of 1, 4-$^{14}$C putrescine into dimethylcasein when the transglutaminase is a component of a bacterial lysate. This is approximately 14 to 21 times the activity shown for the 63 kDa enzyme in Table III of U.S. Pat. No. 5,726,051 issued to Fraij et al. Preferably, the transglutaminase of the present invention has crosslinking activity at least tenfold greater than the activity shown for the 63 kDa protein of Table III in U.S. Pat. No. 5,726,051.

IPTG induction and incubation times for TGC and TGH bacterial expression systems can affect the amount of the conversion to the TG form in the bacterial cells and accordingly the crosslinking activities.

To eliminate the TG isoform formation from the larger precursors which occurs naturally in the bacterial cells, expression vectors containing DNA for TGC, TGH, and TG (as a control) were examined after a short time of IPTG induction (60 min). Lysates from bacterial cells grown under identical expression conditions for these constructs were assayed for crosslinking activities. Only supernatant from the TG isoform was found to contain crosslinking activities. Western analysis of the bacterial expression systems for TGC and TGH showed the presence of the TGC and TGH proteins and that the TG form was not detected. Affinity chromatography purifications of TGC, TGH and TG forms are shown (FIG. 6). The purified TGC and TGH forms did not contain the TG form and assay measurements showed no cross-linking activities, while the purified TG was highly active (Table 3). This proves that the TG isoform is the crosslinking active species and the larger forms (TGC and TGH) are synthesized as inactive zymogens.

The discovery of the active TG forms of human cellular transglutaminase according to this invention reveals for the first time the existence of new forms of TG, which are formed from the inactive larger precursors of cellular transglutaminases. The mass production of the active TG in bacteria, which was purified according to the present invention is shown in Example (3). The enzyme shows substantial stability after several steps of purification, and there was no substantial activity loss after three days incubation at room temperature in elution buffer. This unexpected property for TG enzyme proves to be advantageous for the several usages which include application under bandages, sealant after surgery, inplants, repair of stomach and duedenal ulcers, etc, as other enzymes would lose their activities relatively quickly.

Substantially pure recombinant active cellular transglutaminase of about 50% purity is preferred, at least about 70% is more preferred, and 90–99% or more homogeneity most preferred for food preparations, protein chemistry, therapeutics and other uses apparent to one of skill in the art.

The active human cellular transglutaminase produced according to the present invention finds a variety of uses. For example, active transglutaminase can be used in meat, fish, dairy, vegetable proteins, and miscellaneous applications as shown by eighty five international patents (see generally, Nielson. Food Biotechnology 9: 119–156(1995)).

The active TG of the invention also can be used therapeutically in humans. For example, the transglutaminase has great promise for practical application in clinical orthopedics. The adhesive strength achieved with use of transglutaminase at the cartilage-cartlage interface was greater than that obtained with use of Tissucol, a commercial available fibrin sealant containing a plasma transglutaminase (Jurensen et al. J.Bone and Joint Surgery 79: 155 (1997)). Cellular transglutaminase play an important role in acceleration the formation of a stable dermo-epidermal junction in wound healing (Raghunath et al. L. Clin. Invest. 98: 1174 (1996)).

Cellular transglutaminase crosslinking activities is the subject of U.S. Pat. No. 5,549,904 as a useful tissue sealant and wound formulations. As the active cellular transglutaminase is stable and binds to collagen, it can be used to stabilize basement membrane structures. An appropriate endogenous substrate for the enzyme is fibronectin, which thus serves as a basis for crosslinking and stabilizing collagen/fibronectin complexes, for which the active transglutaminase can be used in the repair of wounds, ulcerated lesions, inplants, tissue or organ transplantations, etc.

The active cellular transglutaminase or its antibodies or the nucleic acids which encode the transglutaminase of the invention can also be used to identify agents which induce or inhibit cellular apotosis. Potential applications for inhibition and induction of apoptosis range from cancer prevention to chemotherapy treatments.

TABLE 3

Transglutaminase activity was determined by the incorporation of 1,4-$^{14}$C-putrescine into dimethylcasein using 1 μg of purified enzyme. A unit of enzyme activity is defined as one μmole of putrescine incorporated per hour of reaction.

| Human transglutaminase isoforms | Specific activity (μmol/mg/h) |
|---|---|
| Bacterially expressed TGC (80 kDa) | 0.00 |
| Human RBC isoforms | 0.64 |
| Bacterially expressed TGH (63 kDa) | 0.00 |
| Bacterially expressed TG (55 kDa) | 11.15 |

EXAMPLE 1

Analysis of Proteolysis Activation of Human Cellular Transglutaminase

Human erythrocyte membranes were isolated from outdated human blood (American Red Cross, Tulsa, Okla.). The cells were washed three times with phosphate-buffered saline (PBS) and then osmotically lysed with three volumes of cold water containing 10 mM $MgCl_2$. The hemolysate was centrifuged for 15 min at 25000×g, and the pellet containing the membranes were suspended in buffer A (50 mM Tris pH 7.5, 150 mM NaCl, 10 mM $MgCl_2$, 1 mM DTT, and 1 mM EDTA).

Isolated membrane proteins (100 μg) were proteolyzed using trypsin (Sigma), at 0.01 mg/ml in buffer A, for the indicated time at 37° C. and then subjected to SDS-PAGE and immunodetection (FIG. 1). For the immunodetection, proteins were transferred by electrophoresis to an Immobilon-P membrane (Millipore) and then detected with rabbit anti-human erythrocyte transglutaminase antibody and a peroxidase conjugated anti-rabbit IgG detection kit (BioRad).

To understand the nature of this cleavage and to confirm the activation process in a human cell system, human RBC and human K562 cells were examined for transglutaminase activation and the effect of time on proteolysis activation of membrane transglutaminase was determined by trypsin treatment. Membrane proteins (100 μg) was incubated with increasing concentrations of trypsin (0, 2.5, 10, 20, and 30 μg/ml) in the presence of 5 mM $CaCl_2$ (o) or 0.3 mM GTP (●) for 1 min at 37 ° C. The proteolysis was inhibited using soybean trypsin inhibitor (0.02 mg/ml) and then one portion of the digested proteins was assayed for transglutaminase cross-linking activity using $^{14}$Cputrescine incorporation for 1 h at 37° C., and another was immediately transferred to SDS-loading buffer and placed in a boiling water bath for 5 min and subjected to SDS-PAGE and immunoblotting to assess transglutaminase activation/cleavage (FIG. 2). Transglutaminase activity was determined by the incorporation of 1,4-$^{14}$C-putrescine into dimethylcasein as described (Lorand et al., Anal. Biochem. 50: 623 (1972)). Briefly, the 200 μl standard reaction mixture contained 20 mM Tris-HCl, pH 7.5, 5 mM $CaCl_2$, 10 mM dithiothreotol, 1 mM putrescine (1.0 μCi/mol), 2 mg/ml dimethylcasein, and 20 μl of supernatant from bacterial lysates (1 μg/1 μl). The reaction mixture was incubated at 37° C. for 1 hr and then terminated by the addition of 2.5 ml of cold 7.5% TCA. The precipitate was collected on Whatman GF/A filters and was washed 3 times with 5 ml cold 5%. TCA. The protein-bound radioactivity was determined in 10 ml Aquasol by liquid scintillation counting. Transglutaminase activation by trypsin proteolysis measured by $^{14}$C-putrescine incorporation was compared to the appearance of a 55 kDa band in immunoblots (FIG. 2). In the presence of calcium ions, or GTP there was an increase in the transglutaminase activity (FIG. 2). Under these assay conditions, transglutaminase had a maximal activation (3 fold) by trypsin after 1 min at 37° C. This resulted in near-complete conversion of TGC (80 kDa) to about a 55-kDa (TG) polypeptide. Longer tryptic digestion resulted in a decrease of enzymatic activity. Complete trypsin inhibition may not have occurred during the activity assay (1 h) which possibly resulted in some degradation of TG species and the decline of activity.

Transglutaminase from the outdated human blood RBC was purified by QA-cellulose and immunoaffinity chromatography as I described earlier (Fraij, Biochem. Biopys. Res. Comm. 218: 45–49 (1996)). Transglutaminase from human RBC (10 μg) was incubated with trypsin (0.01 mg/ml) in buffer A for the indicated time at 37° C. The proteolysis was inhibited using soybean trypsin inhibitor (0.02 mg/ml) and then was subjected to SDS-PAGE and Western blotting. Western analysis showed that the purified TGC was the major form and another species containing a minor 55 kDa form was also present (FIG. 3, lanes 7 and 8).

In the presence of calcium or GTP, trypsin rapidly degraded the purified TGC to low-molecular mass peptides (55-kDa and smaller) (FIG. 3). Thus, membrane association of transglutaminase protected it against rapid degradation.

EXAMPLE 2
Preparation and Cloning of the Active Cellular Transglutaminase Constructs Total cellular RNA was isolated from human white blood cells and from human erythroleukemia K562 cells as described (Birnboim, Nucleic Acids Res 16: 1487–1497 (1990)). Outdated human blood (American Red Cross, Tulsa, Okla.) was centrifuged at 1500×g for 15 min and the interface whitish layer containing white blood cells were removed and used for the total RNA preparations. The isolated human total RNA was amplified by reverse transcription and polymerase chain reaction (RT-PCR). The first strand cDNA was synthesized from twenty µg of the isolated total RNA and 0.5 µg of primer 1 using M-MLV reverse transcriptase or superscript II Rnase H reverse transcriptase kit (Gibco-BRL).

The reaction was incubated at 42° C. for 50 min, heated to 70° C. for 15 min, and placed on ice for 2 min. One-half of the product produced was added directly to PCR reactions with primers 1 and 2, in a final volume of 50 µl. The reaction containing 1.5 mM MgCl$_2$, 0.2 µM dNTP,and 0.8 µM for each primer. Amplification were performed for 30 cycles with 1 minute at 94° C., 2 min at 42° C., and 3 min at 72° C., and a final 7-min incubation at 72° C. Five µl of each reaction was visualized by agarose gel electrophoresis with ethidium bromide staining.

The sequence of primers(P) are:
P1: 5'-TCAGCGGGCACAGAGCAGGA-3' (SEQ ID NO:3).
P2: 5'-CAGGCGTGACGCCAGTTCTAA-3' (SEQ ID NO:4).

Primer 1 is complementary to nucleotides 1547–1564 or 1653–1670 for bovine and human cDNAs. Primer 2 is composed of nucleotides 3–24 for human cDNA.

The unmodified PCR products were directly cloned into T-vectors constructed from EcoRV digested pBluescript (Stratagene) as described previously (Marchuk et al., Nucleic Acids Res. 19: 1154 (1991)). White colonies were chosen by color detection to make mini preparation from liquid culture. Size of E.coli plasmids were examined as described previously (Akada, BioTechniques 17:1, 58 (1994)). Digested DNA plasmids were fractionated on 1% agarose, and positive clones which showed the expected DNA insert size of about 1.6 kb were examined by DNA sequencing. Sequence analysis confirmed the nucleotide sequence of the designed cDNA construct as shown in FIG. 1 and SEQ ID NO:1. Constructs with the following carboxyl terminal ends were synthesized as above and using specific primers. Lysine 464, glycine 480 and proline 446 carboxyl terminal constructs were amplified by using primer 2 and primer 3, 4, or 5 respectively. For cloning purposes primer 2 was substituted with primer 6 or 7, and the PCR products were cloned as mentioned earlier.

The sequences of the specific primers are:
P3: 5'-TCATTTGTTCAGGTGGTT-3' (SEQ ID NO:5),
P4: 5'-TCAGCCCACACGGATCCGCAT-3' (SEQ ID NO:6),
P5: 5'-TCATGGGTATTTGTAGGTGTG-3' (SEQ ID NO:7)
P6: 5'-ACCTCCTTAAAGCATAAATCTCA-3' (SEQ ID NO:8)
P7: 5'-ATGGCCGAGGAGCTGGT-3' (SEQ ID NO:9)

At the 5'-end of primers 3,4,5 and 7 sequences containing NdeI and or XhoI restriction sites were added for cloning purposes. Primers 3, 4, and 5 are complementary to nucleotides (1472–1487 or 1511–1526), (1468–1486 or 1556–1574) and (1366–1384 or 1452–1470) for bovine and human cDNAs. Primer 6 is composed of nucleotides 80–103 of human cDNA and primer 7 is composed of nucleotides 35–62 or 135–156 for bovine and human cDNAs. Bovine and human cellular transglutaminase cDNA sequences were published previously. (Nakanishi et al., Eur. J. Biochem. 202: 15–21 (1991), and Gentile et al., J. Biol. Chem. 266: 478–483 (1991)).

Plasmid DNA was prepared and purified by polyethylene glycol precipitation. Double stranded plasmid DNA was used for sequencing on an Applied Biosystem model 373 DNA sequencer using a fluorescent dye labeled dideoxy terminator kit (Applied Biosystem Inc.) and Taq polymerase. Comparison of deduced amino acid sequences between the active cellular transglutaminase reported in this invention and the larger TGH and TGC shows almost an identity. The active site Cysteine (277) and the putative calcium binding region between amino acids 446–453 were present. Few base changes were found in the constructs, these changes possibly are a combination of polymorphisms, ambiguities in sequencing and PCR errors. As an example, two base changes were found in construct Gly 480 resulting in two amino acid changes located at amino acid positions 250 (Ser/Arg) and 394 (Phe/Ser), and in spite of a charged arginine at position 250, which is close to the cysteine 277 of the active site region, the expressed transglutaminase was active enzyme. Therefore, base changes which do not include cysteine 277 directly appear to be harmless.

For cloning the full length TGC which codes for 687 amino acids, primer 6 and primer 8 were used in RT-PCR amplifications of the isolated total RNA as described above. Primer 8 sequence is: 5'-CCCTTAGGCGGGGCCAA-3' (SEQ ID NO:10). Primer 8 is complementary to nucleotides 2096–2113 and 2185–2202 of bovine and human cDNAs. For cloning purposes sequences containing NdeI and or XhoI restriction sites were added to the 5'-end of primer 8. TGH cDNA is available from my previous work as mentioned earlier.

EXAMPLE 3
Expression and Purification of the Transglutaminase Isoforms and Antibody Purification Two expression vectors were used: 1-pET-14b (Novagen) which constructed to produce the exact transglutaminase sequences (native) and 2-pRSET B (Invitrogen) which produces an N-terminal 4.8 kDa leader peptide containing histidine tag for purification purposes. Both plasmids contain T7 promoter and a transcriptional terminator to drive expression of the transglutaminase forms in E coli. Plasmids containing TGC, TGH, TG (Lys 464 or Gly 480 constructs), TG446, and TG512 and pET-14b DNAs were digested with two restriction enzymes, NcoI and XhoI for 1 h. Plasmids containing TGC, TGH, and TG and PRSET-B DNA were digested with NcoI and HindIII. The DNA inserts for the transglutaminase forms and the digested DNA plasmids were purified from 1% agarose gel.

The purified pET DNA was added to purified DNA for TGC, TGH, TG, TG446, and TG512 separately and the purified pRSET DNA was added to DNA for TGC, TGH, and TG separately and then each reaction was ligated by T4 DNA ligase as recommended by manufacturer (Gibco-BRL).

pET or pRSET containing transglutaminase cDNA were prepared and purified from minipreparations and then introduced into E. coli BL21 (Novagen) bacterial cells. Cells containing the transglutaminase-expression vector were grown in LB or TB with ampicillin or carbenicillin (50 μg/ml) at 37° C. At 0.6 $A_{595}$ nm, induction of expression was initiated by adding isopropyl β-D-thiogalactoside (IPTG), to a final concentration of 0.2 mM. Cells were harvested 1–5 h later and resuspended in 0.02 M Tris-HCl, pH 7.5, 0.5 mM dithiothreitol (DTT), 1 mM phenylmethylsulfonyl fluoride (PMSF), 1 mM EDTA, and 0.5% Triton X-100. Bacterial cells were lysed by sonication at 4° C. and centrifuged for 10 min at 15000×g. Supernatants were used for crosslinking activity measurements and Western analysis.

Western analysis of supernatants from the bacterial pRSET (TGC and TGH) expression systems which were induced for 3–5 h showed that some of TGC and TGH proteins were converted to TG form as indicated by the top arrow (FIG. 4), and these samples when assayed showed crosslinking activities (Table 1). Bacterial pET (TGC and TGH) expression samples showed weak conversions of the TGC and TGH to the TG form as indicated by the bottom arrow (FIG. 4, lanes 5 and 6), and assay measurements of these samples produced low crosslinking activities (Table 2). Bacterially expressed TG from pRSET and pET systems produced high crosslinking activities. The presence of the leader peptide at the N-terminal from the pRSET expression system did not lower drastically the crosslinking activity when compared with the native forms produced by the pET expression system. TG446, TG512 expression products (FIG. 4) produced very weak crosslinking activities when compared to TG activity (Table 2). The incubation and IPTG induction times for TGC and TGH bacterial expression systems can affect the amount of the conversion to the TG form and accordingly the crosslinking activities.

For affinity purifications, Histidine Tag resin affinity purification of recombinant transglutaminase was performed as described by manufacturer (Novagen). Briefly, cells from short IPTG induction (1 h) cultures were suspended in 4 ml cold binding buffer (5 mM imidazole, 0.5M NaCl, 0.1% TritonX-100, and 20 mM Tris-HCl pH 7.9). Cells were broken by sonication until the sample was no longer viscous. Lysates were centrifuged at 15000×g for 10 min and supernatant was filtered through a 0.45 micron membrane. Supernatants were assayed for crosslinking activity, western analysis and/or applied to a His Tag column.

Supernatant samples loaded onto a column containing 3.0 ml His Tag resin, equilibrated with 25 ml binding buffer and the column was washed with 15 ml of wash buffer (60 mM imidazole, 0.5M NaCl, and 20 mM Tris-HCl pH 7.9). Enzymes was eluted with 10 ml of 1M imidazole, 0.5M NaCl, and 20 mM Tris-HCl pH 7.9, and enzyme fractions were concentrated to a protein concentration of 2.0–2.5 mg/ml, and stored at −20° C. Purified transglutaminase isoforms were subjected to SDS-PAGE using 10% acrylamide minislab gel system. Equal amounts of TG (lanes 1, 4, and 7), TGH (lanes 2, 5, and 8), and TGC (lanes 3, 6, and 9) were used. Proteins were transferred by electrophoresis to Immobilon-P membrane. The membrane was cut into three parts A, B, and C and each was probed separately with the specific affinity purified antibody. Western analysis and Coomassie Brilliant Blue (CBB) staining of the purified TGC, TGH, and TG from the bacterial expression systems are shown (FIG. 6). Assay measurements of the crosslinking activities are presented in Table 3.

Antibody purification: the antibody was prepared by mixing 1 mg of affinity purified TGC from human RBC or 5 mg of purified recombinant TG polypeptide. Proteins were dissolved in sterile saline and emulsified with 5 ml of complete Freund's adjuvant. Female New Zealand rabbits were injected with 1 ml of the emulsion subcutaneously. Three subsequent booster injections were given later. Serum was tested for antibodies using Western blots. A 2-cm high Ni-NTA column (Qiagen) purification procedure was used as described (Gu et al, BioTechniques 17: 257–262 (1994)). Briefly BL-21 transformed bacteria with pRSET plasmid containing TG cDNA were grown as described above. Cells were lysed in 6 M guanidine HCl, 0.1 M Na-phosphate, 0.01 M Tris-HCl pH 8, and 10 ml of the extract were applied to the Ni-NTA column equilibrated in the same buffer. The column was washed in lysed buffer and in buffer containing 8 M urea, 0.1 M Na-phosphate, 0.01 M Tris-HCl pH 8, pH 6.3 and pH 5.9 consecutively. The column was equilibrated in 0.15 M NaCl, 0.05 M Tris-HCl, pH 7.4 for application of the antiserum samples. The serum (2 ml) from rabbits injected with either RBC purified TGC or the bacterially produced recombinant forms was applied to the column and washed with 5×column volumes of 150 mM NaCl equilibrating buffer, followed by 5×column volumes of 2 M NaCl, 50 mM Tris-HCl, pH 7.4. The antibody was eluted with 4 M $MgCl_2$ (no buffer). The eluted antibody was dialyzed against PBS exhaustively at 4° C. and then stored at −20° C. The purified antibody was found effective in immunodetection at a dilution of 1:5000 (volume to volume), as shown in FIG. 4.

The invention further comprises a cultured cell line transformed or transfected with a recombinant DNA construct consisting essentially of a sequence encoding amino acids 1–448 to 1–510 of SEQ ID NO:2. The transglutaminase enzyme has crosslinking activity which is at least about ten to 14 to 21 fold greater than a transglutaminase enzyme having a molecular weight of about 63 kDa. Said cultured cell line may be a bacterial cell line. Said recombinant DNA construct may be pRSET or pET. Further, the recombinant DNA construct may be linked to at least one sequence from a bacteriophage. In a preferred process, the transformed bacterial cell is cultivated, after which the transglutaminase is isolated from the cells.

From the foregoing it will be appreciated that, although specific embodiments of the invention have been described herein for purposes of illustration, various modifications may be made without deviation from the principle, fundamental, and scope of the invention. Accordingly, the invention is not limited except as by the appended claims.

What is claimed is:

1. A purified transglutaminase enzyme comprising at least amino acid residues 1–448 of SEQ ID NO:2 and truncated at a residue of SEQ ID NO:2 between residue 448 and residue 510 inclusive, wherein the transglutaminase enzyme has crosslinking activity which is at least about fourteen fold greater than the transglutaminase enzyme TGH having a molecular weight of about 63 kDa.

2. The purified transglutaminase enzyme of claim 1 having a molecular weight of about 51 to about 58 kilodaltons as estimated by SDS-PAGE.

3. The purified transglutaminase enzyme of claim 1 having a molecular weight of about 53 to about 57 kilodaltons as estimated by SDS-PAGE.

4. The purified transglutaminase enzyme of claim 1 having a molecular weight of about 55 kilodaltons as estimated by SDS-PAGE.

5. A purified transglutaminase enzyme encoded by a recombinant DNA construct consisting essentially of a sequence encoding at least amino acids 1–448 of SEQ ID NO:2 and further up to and including amino acids 1–510 of SEQ ID NO:2 and wherein the transglutaminase enzyme has crosslinking activity which is at least about fourteen fold greater than the transglutaminase enzyme TGH having a molecular weight of about 63 kDa.

6. The transglutaminase enzyme of claim 5 wherein the recombinant DNA construct further comprises a transcriptional promoter and a transcriptional terminator.

7. The purified transglutaminase enzyme of claim 5 having a molecular weight of about 51 to about 58 kilodaltons as estimated by SDS-PAGE.

8. The purified transglutaminase enzyme of claim 5 having a molecular weight of about 53 to about 57 kilodaltons as estimated by SDS-PAGE.

9. The purified transglutaminase enzyme of claim 5 having a molecular weight of about 55 kilodaltons as estimated by SDS-PAGE.

10. A purified transglutaminase enzyme comprising at least amino acid residues 1–448 of SEQ ID NO:2 and truncated at a residue of SEQ ID NO:2 between residue 448 and residue 510 inclusive, wherein the transglutaminase enzyme has crosslinking activity of at least about 1000 cpm/hr/$\mu$g of bacterial lysate where crosslinking activity is based on incorporation of 1,4-$^{14}$C putrescine into dimethylcasein.

11. The purified transglutaminase enzyme of claim 10 having a molecular weight of about 51 to about 58 kilodaltons as estimated by SDS-PAGE.

12. The purified transglutaminase enzyme of claim 10 having a molecular weight of about 53 to about 57 kilodaltons as estimated by SDS-PAGE.

13. The purified transglutaminase enzyme of claim 10 having a molecular weight of about 55 kilodaltons as estimated by SDS-PAGE.

* * * * *